(12) United States Patent
Mueller

(10) Patent No.: US 6,882,426 B1
(45) Date of Patent: Apr. 19, 2005

(54) GAS SENSOR WITH SLOTTED DIFFUSIVE GAS SAMPLE CHAMBER

(75) Inventor: Michael M. Mueller, Portland, OR (US)

(73) Assignee: Digital Control Systems, Inc., Portland, OR (US)

( * ) Notice: Subject to any disclaimer, the term of this patent is extended or adjusted under 35 U.S.C. 154(b) by 289 days.

(21) Appl. No.: 10/183,921

(22) Filed: Jun. 26, 2002

(51) Int. Cl.[7] .................. G01N 21/01; G01N 21/61
(52) U.S. Cl. ........................ 356/440; 356/437
(58) Field of Search .................. 356/436, 440, 356/246, 437–439; 250/343

(56) References Cited

U.S. PATENT DOCUMENTS

| | | |
|---|---|---|
| 3,702,397 A | 11/1972 | Firth et al. |
| 4,323,777 A | 4/1982 | Baskins et al. |
| 4,662,755 A | 5/1987 | Aoki et al. |
| 5,125,742 A | 6/1992 | Wilks, Jr. |
| 5,163,332 A | 11/1992 | Wong |
| 5,874,737 A * | 2/1999 | Bytyn et al. .......... 250/343 |

* cited by examiner

Primary Examiner—Richard A. Rosenberger
(74) Attorney, Agent, or Firm—Marger Johnson & McCollom, P.C.

(57) ABSTRACT

A diffusion-type gas sensor is disclosed. The sample chamber uses a narrow slot as a gas diffusion port. The slot is advantageous as it can be formed during extrusion of chamber stock material, instead of during subsequent machining steps that are costly and may adversely affect the chamber surfaces. Further, the slot profile can be designed according to various profiles and/or positions that can improve gas diffusion, chamber reflection efficiency, or both, as compared to conventional ported chamber designs.

22 Claims, 6 Drawing Sheets

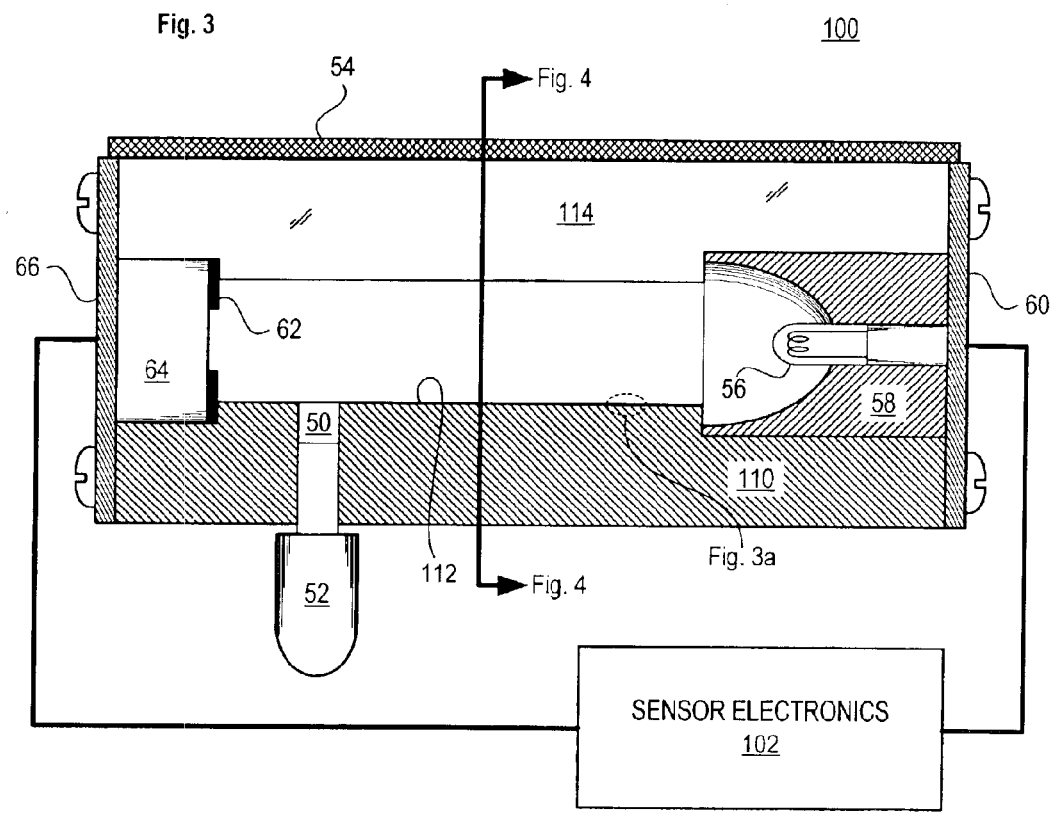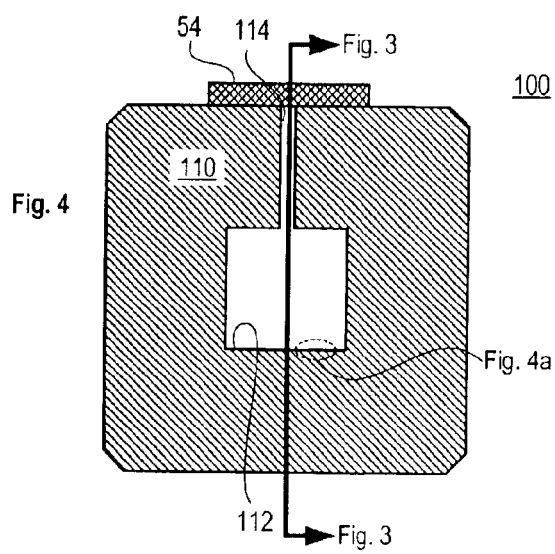

GAS SENSOR WITH SLOTTED DIFFUSIVE GAS SAMPLE CHAMBER

FIELD OF THE INVENTION

This present invention relates generally to gas sensors, and more specifically to a gas sensors having sample chambers for non-dispersive infrared measurement of gas concentration.

BACKGROUND OF THE INVENTION

Many techniques exist for measuring the concentration of a constituent gas or gases in a gas sample. Non-dispersive infrared (NDIR) techniques infer the concentration of a constituent gas by measuring a gas sample's ability to absorb electromagnetic radiation. By examining absorption in a wavelength band where absorption is dominated by one constituent gas, relatively simple NDIR sensors can accurately measure concentration of that gas as a function of radiation absorption. For instance, carbon dioxide ($CO_2$) detectors often measure absorption at a 4.2-micron wavelength, where $CO_2$ strongly absorbs. For other gases, other visible or infrared bands can be selected.

With appropriate focusing optics, free-air absorption of atmospheric gases is possible. Nevertheless, most environmental NDIR sensors utilize enclosed gas sample chambers to, e.g., enhance the signal received at the detector, prevent contamination of the optical components, ruggedize the device, make the device smaller and more portable, etc.

FIG. 1 illustrates a typical prior art gas sample chamber 10, similar to that disclosed in U.S. Pat. No. 5,163,332, issued Nov. 17, 1992, to Wong. Chamber 10 comprises a specularly reflective tube 12 with a source 16 (e.g., an incandescent bulb) at one end and a radiation detector 18 at the opposite end. An array of circular apertures 20, drilled along tube 12, allows gas to enter and exit chamber 10. Each aperture is covered by a semipermeable membrane 22 that filters particles down to at least 0.1-micron particle sizes, to prevent those particles from entering the chamber and diminishing the critical reflectivity of inner chamber surface 14.

As is typical in the prior art, the mirrored chamber walls of tube 12 act as a light pipe, guiding radiation, emitted by source 16, down to detector 18. Light ray 24 represents a boresighted light ray that passes directly from source 16 to detector. Light rays 26, 28, and 30 represent light emitted at increasing angles of deflection, as measured from the boresight angle. Ray 26 reflects once off of the tube wall—with a tube aspect ratio of 12:1, ray 26 has a deflection angle of about 4.8 degrees. Ray 28 reflects twice off of the tube wall—with the same tube aspect ratio, ray 28 has a deflection angle of about 9.5 degrees. Ray 30 reflects three times off of the tube wall, and has a deflection angle of about 14 degrees. Higher-order reflections are possible, but tend to be less effective, due primarily to the difficulty of avoiding intersection with one or more of the apertures 20 (which do not propagate light forward) as well as diffusive and reflectivity losses that multiply with repeated reflection. Accordingly, most of the light that reaches detector 18 emanates from source 16 within about a plus-or-minus 14-degree cone surrounding the boresight angle.

A competing sample chamber 40, designed by the inventor of the present invention, is shown in FIG. 2. Instead of an elongated tube, chamber 40 has a relatively short aspect-ratio (e.g., 4:1), and is formed in a relatively thick-walled stock material 42. Four gas ports 44, 46, 48, and 50 are bored through the chamber walls, two near the source and two near the detector. Port 50 is used for injection of calibration gas, and is nominally blocked by cap 52. Ports 44, 46, and 48 allow different two- and three-port forced-flow and gas diffusion configurations—a three-port gas diffusion configuration is shown. Each open port is covered with some sort of porous media 54 to prevent insects, spiders, gross dust, and large solid objects from entering chamber 40.

Sample chamber 40 accepts a source assembly, comprising incandescent bulb 56, elliptical reflector 58, and mounting plate 60, into a machined hole in one end. Chamber 40 accepts a detector assembly, comprising an aperture stop 62, a detector 64, and a mounting plate 66, in a second machined hole in its opposite end.

One significant difference between light pipe chamber 10 and chamber 40 is the surface finish of the inner chamber. Instead of a mirror surface, chamber 40 incorporates an inner surface 68 that is relatively rough compared to radiation at wavelengths of interest. During fabrication, the surface roughness and stability are enhanced by a surface etch and a yellow chromate step.

SUMMARY OF THE INVENTION

Although the gas sample chamber of FIG. 2 improves upon the chamber of Wong in size (FIGS. 1 and 2 are not drawn at the same scale), simplicity, ruggedness, and at least some aspects of signal stability, some of the reasons for these improvements were previously unappreciated. The present disclosure draws upon new insights gained through experiments in optical transmission, surface roughness, and diffusion properties, to further improve upon the design of a simple gas sample chamber based on the chamber of FIG. 2.

One of the problems Wong and those who came before him struggled with was how to allow gas to diffuse into the chamber at a sufficiently high rate, without either allowing contaminants into the chamber or significantly decreasing the reflective surface of the chamber by placing too many (or too large) holes in it. Wong selected thin membranes, also used by several previous designs, to provide decent gas transport and fine filtering. Wong used relatively tiny holes to avoid diminishing light reflectivity too much. And although this feature was not part of Wong's patent, observation of Wong's commercial devices leads to the conclusion that his hole pattern was critical, and designed to allow major reflective modes to miss his gas apertures.

The sample chambers according to a first aspect of the present invention, while delivering radiation amounts comparable to Wong's device, takes an entirely different approach to radiation delivery. Instead of a long, narrow light pipe, these embodiments of the present invention use a relatively short sample chamber with a roughened inner surface. The roughened inner surface tends to propagate radiation generally down the chamber, but spreads the radiation so that much more of the chamber contributes to single-bounce reflections, instead of the relatively small chamber regions relied on in a long light pipe chamber. Thus whether particular points on the chamber surface achieve optimal reflectivity can be less of a critical concern.

Gas enters and exits the chamber through a slot along the long dimension. The slot allows gas to diffuse more evenly along the length of the chamber, preferably providing improved diffusion. Further, the slotted design can provide simplified fabrication, particularly when the chamber is formed from extruded stock: the gas port requires no fabrication steps such as drilling, and can be shaped to provide more surface area at the porous media than at the inner chamber wall.

Some aspects of the present invention can also be incorporated into light pipe-type chambers. For instance, the slot can be made quite narrow at the inner chamber surface, and still allow gas exchange at a rate comparable to an ultra-fine filter while only insubstantially decreasing the efficiency of the light pipe: in fact, the slot can be tapered towards the inner chamber surface such that a greater surface area of the filter is available to increase the diffusion rate. Another aspect, useful with thick-walled chambers, is a slot that enters the sample chamber at an angle to the surface normal, such that the slot itself can be largely hidden from radiation that is meant to be contained within the chamber.

BRIEF DESCRIPTION OF THE DRAWING

The invention may be best understood by reading the disclosure with reference to the drawing, wherein:

FIGS. 3 and 4 show two cross-sectional views of a gas sensor according to one embodiment of the present invention;

DETAILED DESCRIPTION OF THE EMBODIMENTS

Figure 1:
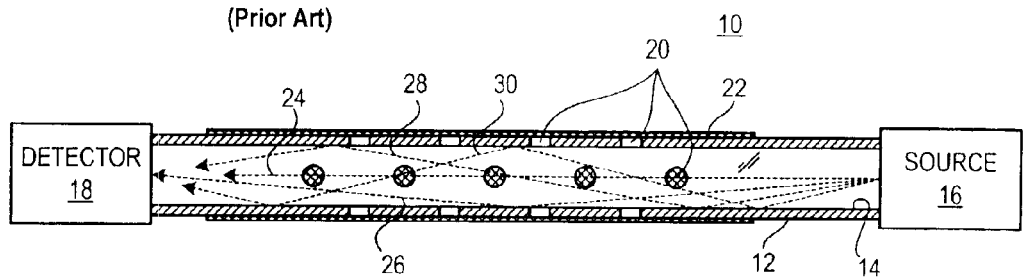
FIG. 1 illustrates in cross-section a prior art long light pipe-type NDIR gas sensor.

FIG. 3 shows a gas sensor 100 according to one embodiment of the present invention. Calibration port 50, bulb 56, reflector 58, mounting plate 60, aperture 62, detector 64, and mounting plate 66 can be identical to the corresponding elements of FIG. 2. Electronics 102 drives the source, receives measurements from the detector, and provides other ancillary monitor functions such as display, calibration, the generation of control signals, etc., as is well known in the art.

Sample chamber 110 is shown in cross-section along the direction of light propagation in FIG. 3, and in cross-section perpendicular to the direction of light propagation in FIG. 4 (the bulb and detector are not cross-sectioned, and are omitted from FIG. 4 for clarity). Chamber 110 is preferably formed of extruded 6063-T6 aluminum chamber stock. Although the extrusion parameters can vary widely, it is preferable that the die be allowed to leave die marks along the inner surface of the chamber blank. These marks score the surface along the direction of light propagation. The die is patterned to form a narrow slot 114 along the chamber blank as the blank is extruded, the slot extending from the outer surface of the blank to one inner chamber wall. This slot will serve as the gas diffusion port in the final assembly.

In some embodiments, the extruded chamber walls are relatively thick, e.g., half as thick (or thicker) than the width of the inner chamber opening. This thickness provides structural support for the chamber to prevent deformation. In particular, the chamber wall opposite the slot can be thickened to resist bending moments. As will be seen, additional thickness also makes it easier to design innovative slot designs that improve diffusion, chamber reflection efficiency, or both.

Figure 2:
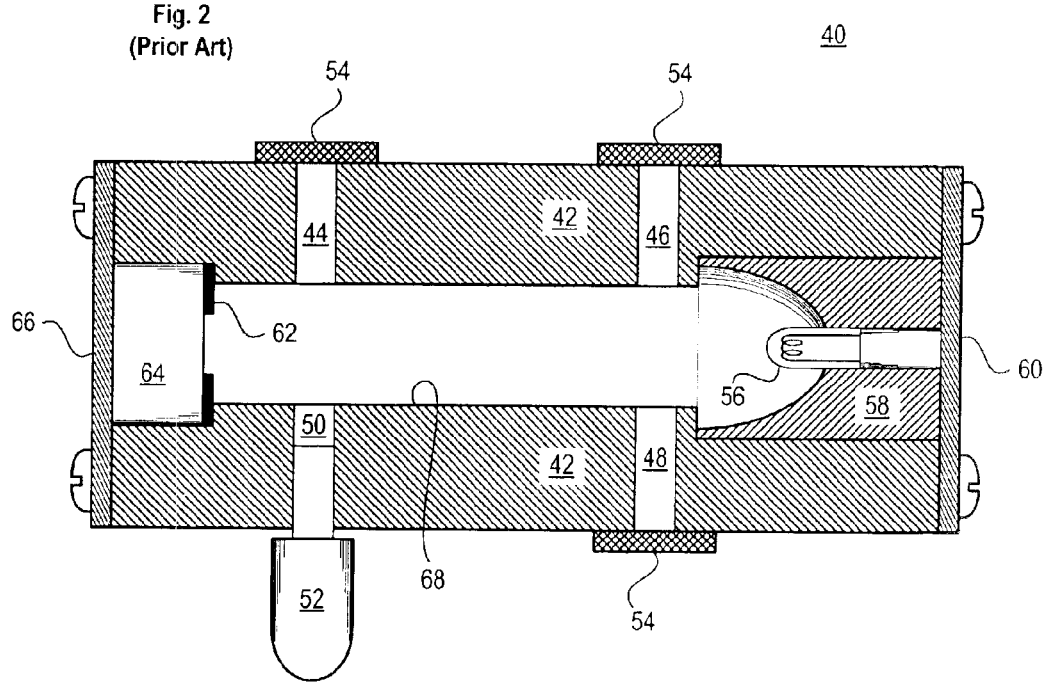
FIG. 2 illustrates in cross-section a shortened NDIR gas sensor that is a precursor in some aspects to the embodiments described herein.

The slot can be quite narrow in practice. For instance, the chamber section of the device illustrated in FIG. 2 is approximately 1.1 inches long, and the ports 44, 46, and 48 have a 0.18-inch diameter. The cross-sectional area available for gas diffusion with three ports is approximately 0.076 $in^2$. With a $1/16$-inch-wide slot 114, the available cross-sectional area is approximately 0.069 $in^2$. The porous media 54 covers a slot with a larger cross-sectional area, however, approximately 0.1 $in^2$ or greater. If the porous media limits the gas exchange rate (as it typically will), the narrow slot with less area at the inner chamber wall will actually respond quicker to changes in gas concentration than the drill-ported version. Further, the multi-ported chamber must rely to a greater extent on gas mixing within the chamber itself.

Once the chamber blank has been extruded, cut to an appropriate length, and machined to accept the calibration port, source, and detector, it is subjected to an etch and chromate process. The blank is first cleaned by a hot soapy water wash, a chromic acid dip, and a rinse. The blank is then etched by immersion in a tank containing a sodium hydroxide solution for two to three minutes, depending on the concentration of the solution. The immersion time is set to remove approximately 0.0008 to 0.001 inches of material from the chamber surfaces. The blank is then rinsed, dipped in chromic acid again to remove sodium hydroxide residue, and rinsed again. The blank is then dipped in a chromate conversion tank to form a Class 3 coating according to Military Specification MIL-C-5541. Reaction time is determined visually by the tank operator, i.e., the blanks are left in the tank until their surfaces appear dark yellow to light brown. The yellow indicates that unreacted chrome remains on the surface. The etch-chromate process slightly roughens the chamber surface, and imparts corrosion resistance to the aluminum.

After processing, the chamber inner surface 112 is neither specular nor completely diffuse, but something in between. (As the term is used herein, a "specular" surface requires that the average peak-to-peak surface roughness not exceed $1/10$ of a wavelength for the light under consideration. A "diffuse" surface scatters light with no preferred direction.) This surface is thus non-specular, but still generally directs radiation traveling forward down the chamber (i.e., hitting the chamber surface at glancing angles) in a forward going, but spread, reflective pattern.

Figure 3A:
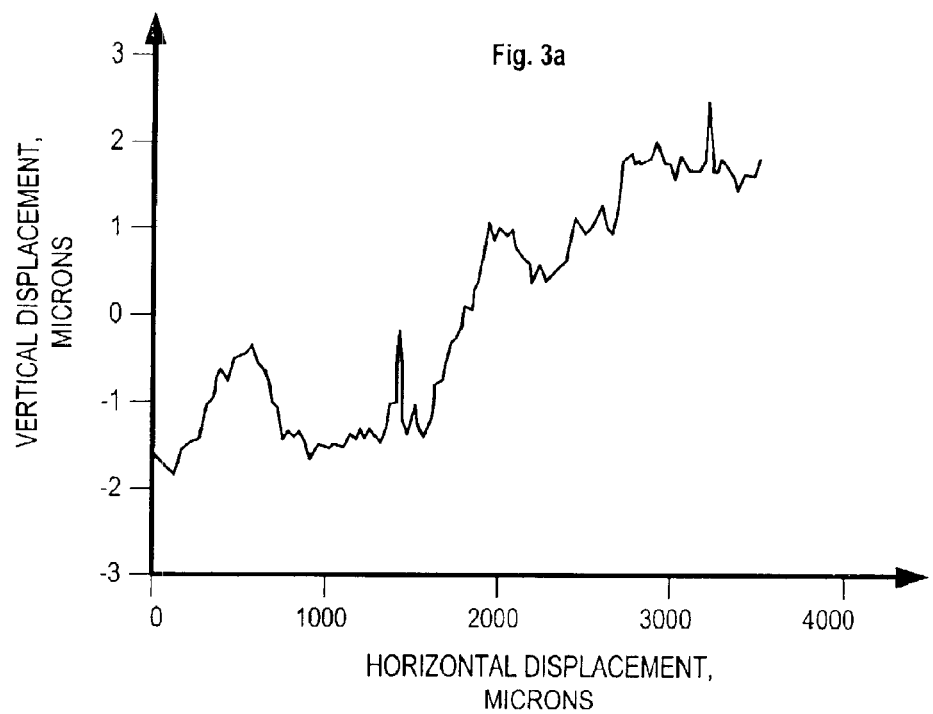
FIGS. 3a and 4a plot surface roughness in two different directions for the inner chamber surface of the chamber shown in FIGS. 3 and 4.
Figure 4A:
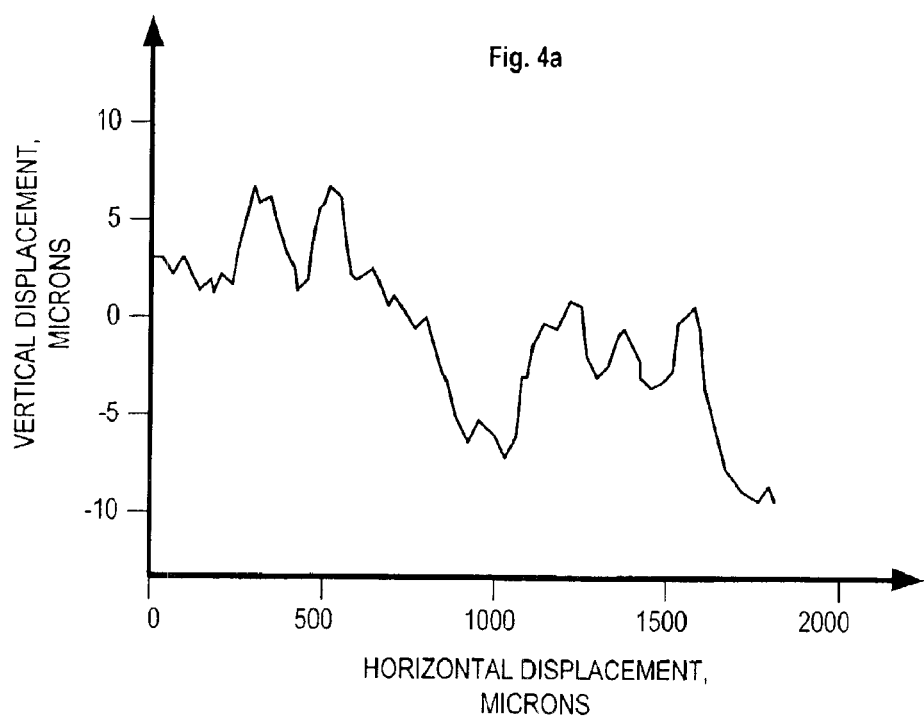

One particular roughness found to work well for $CO_2$ detection is typified by the surface roughness plots of FIGS. 3a and 4a. FIGS. 3a and 4a plot profilometer measurements taken on an inner chamber surface in two perpendicular directions. FIG. 3a shows typical roughness measured along the long axis of the chamber, with an average peak-to-peak roughness of less than about 2 microns. FIG. 4a shows typical roughness measured perpendicular to the long axis of the chamber, with an average peak-to-peak closer to 5 microns. Additionally, the roughness of FIG. 4a is more correlated than the roughness of FIG. 3a, that is, the roughness generally represents persistent score marks along the chamber.

In operation, it is believed that this preferentially roughened surface efficiently forward-scatters a significant fraction of radiation hitting the surface at shallow grazing angles, e.g., 5- to 15-degree angles. For instance, in a test using a laser source directed at an inner chamber surface, the laser beam was forward scattered fairly uniformly over about a 20-degree solid angle, with small amounts of radiation backscattered.

Figure 5A:
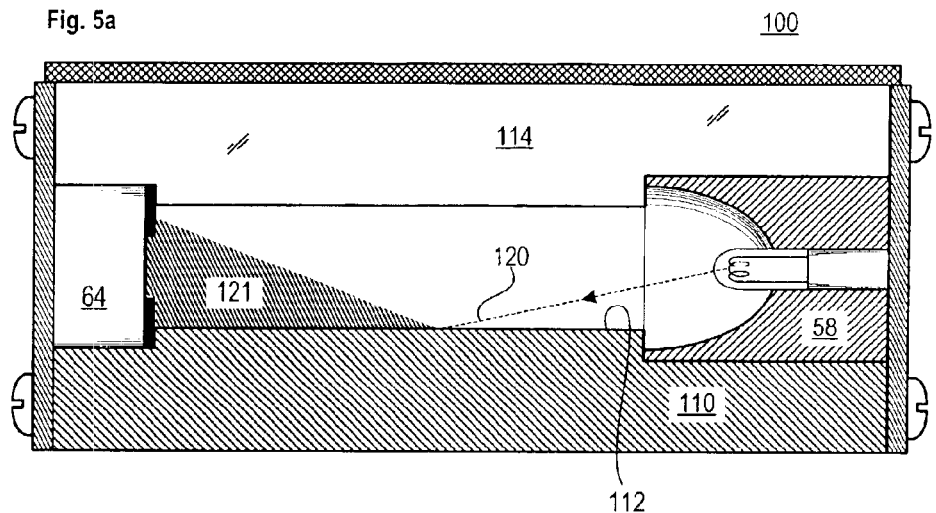
FIGS. 5a, 5b, and 5c show, for one embodiment, approximately how radiation is guided through a chamber.
Figure 5B:
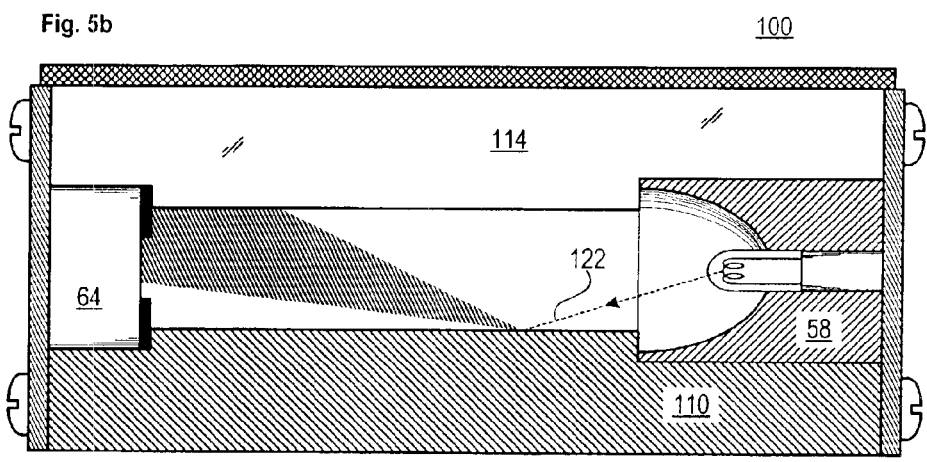
Figure 5C:
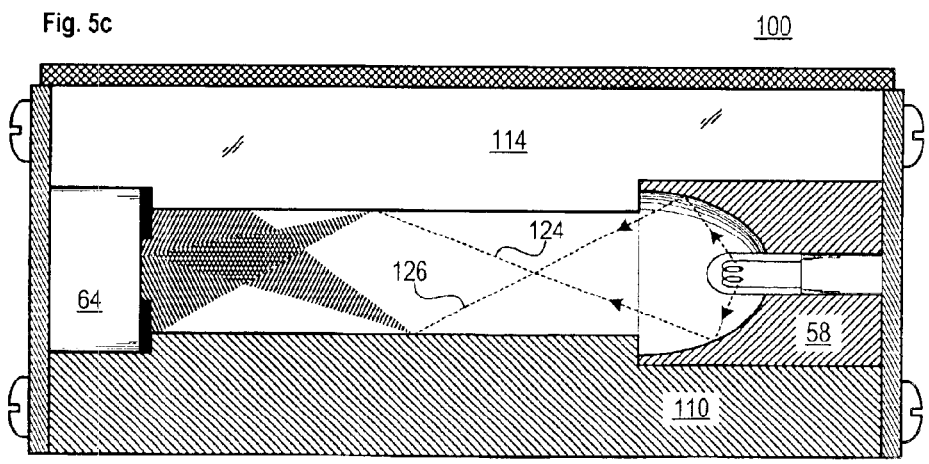

The manner of light transmission achieved with the preferentially roughened surface can be starkly different from that achieved with a specularly reflective surface. For instance, FIGS. 5a, 5b, and 5c show light rays emanated from the source at several different angles. Was the surface specularly reflective, only light ray 120 would reflect to the detector, and rays 122, 124, and 126 would strike the aperture stop. Light ray 120 would illuminate a single spot on the detector 64. But with the preferentially roughened surface, light ray 120 scatters into a broadened light packet 121 upon hitting surface 112, and thus is believed to more uniformly illuminate the surface of detector 64 (some of the scattered light misses the detector). But light ray 122 is now partially scattered onto detector 64, whereas in a specular chamber that ray would not contribute to the detector reading. Further, bulb 56 is located near the focus of elliptical reflector 58. Light rays 124 and 126 reflect off of the elliptical reflector 58 and cross near the second focus of the elliptical reflector, forming a "virtual" source at that location. This virtual source also creates spread reflections off of the chamber wall, as shown in FIG. 5c.

Effectively then, no point on the chamber surface 112 is as critical as with a specular chamber, as the surface "averages" the illumination. And more points on the surface actually contribute to the detector signal, as compared to a specular chamber.

It is now believed that this forward-scattering surface gives several advantages. First, if some particles deposit on the surface, these particles should not appreciably change the signal received at the detector—the surface is already rough, and light is already scattered. Likewise, although the yellow chromate surface is fairly inert, some corrosion of the surface will make little appreciable difference. And if thermal or mechanical forces slightly distort the chamber, this will not change the detector signal the way it might with a specular surface, where small thermal changes may cause significant shifts in the light pattern that is mirror-reflected to the detector.

Accordingly, the porous material 54 covering the gas port need not provide ultrafiltration, as it should with a specular chamber. A looser filtering requirement can allow the diffusive area of the porous material to be reduced (or response time to be reduced), since a loose filter generally does not provide the same impediment to gas transport as a submicron filter might. Indeed, one embodiment uses Vent Tape 394 (a trademark of 3M), a loosely matted-fiber gas-permeable tape, which can simply be taped over the outer surface of chamber 100 to cover slot 114. Of course, those skilled in the art recognize that a multitude of porous materials are available to accomplish (or over-accomplish) the same purpose, including sub-micron filters and membranes.

Figure 6:
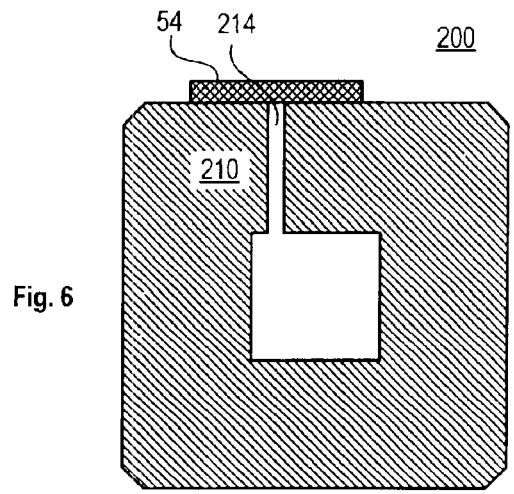
FIGS. 6, 7, 8, and 9 show chamber cross-sections for alternate embodiments.

In FIG. 4, the slot is centered on one wall. FIG. 6 shows an alternate embodiment that places the slot off-center, which may increase the amount of radiation reaching the detector (it is believed that points near the center of a square-chamber wall contribute more to the detector signal than those further off-center).

Figure 7:
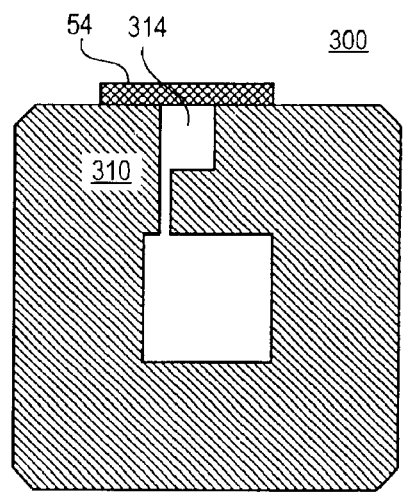
Figure 8:
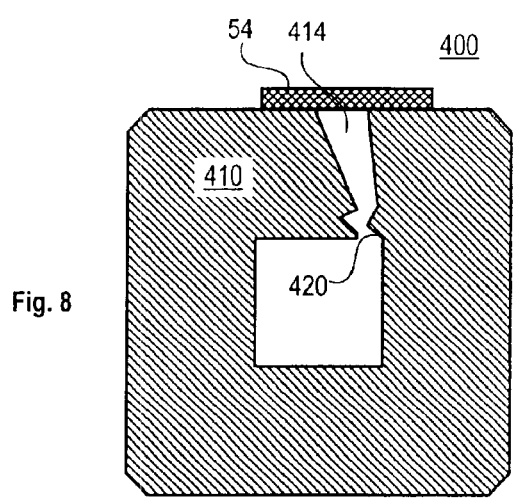

FIG. 7 shows yet another embodiment where the slot width varies with depth. At the inner chamber surface, slot 314 is at its narrowest, and thereby leaves most of the inner chamber surface available for reflection. At the outer chamber surface, slot 314 is at its widest, allowing the porous material to diffuse gas through a greater surface area. Even with a narrower cross-section at the inner chamber surface than slot 214 (FIG. 6), the diffusion rate may be no worse (or even better) than the slot of FIG. 6. Such a slot embodiment could be used to advantage with a light-pipe chamber to improve reflectivity and diffusion at the same time.

The particular slot profile shown in FIG. 7 could be machined as well as extruded. Other varying-profile slots could include continuously tapered slots that are more amenable to extrusion.

Figure 9:
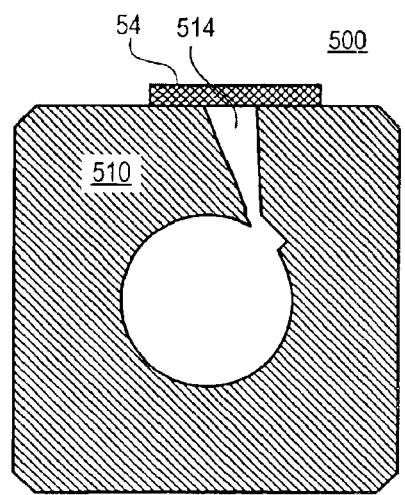

FIG. 9 shows a more circuitous slot profile 414. Such a profile can be designed to bounce light that enters the slot back into the chamber and towards the detector, even further diminishing light loss due to the gas port. For instance, wall 420 of slot 414 can be canted to be approximately normal to source radiation that hits that surface directly, thereby bouncing that radiation generally towards the detector. Such a design can have almost no reflective efficiency penalty, and is therefore useful as well in light-pipe chambers.

Figure 10:
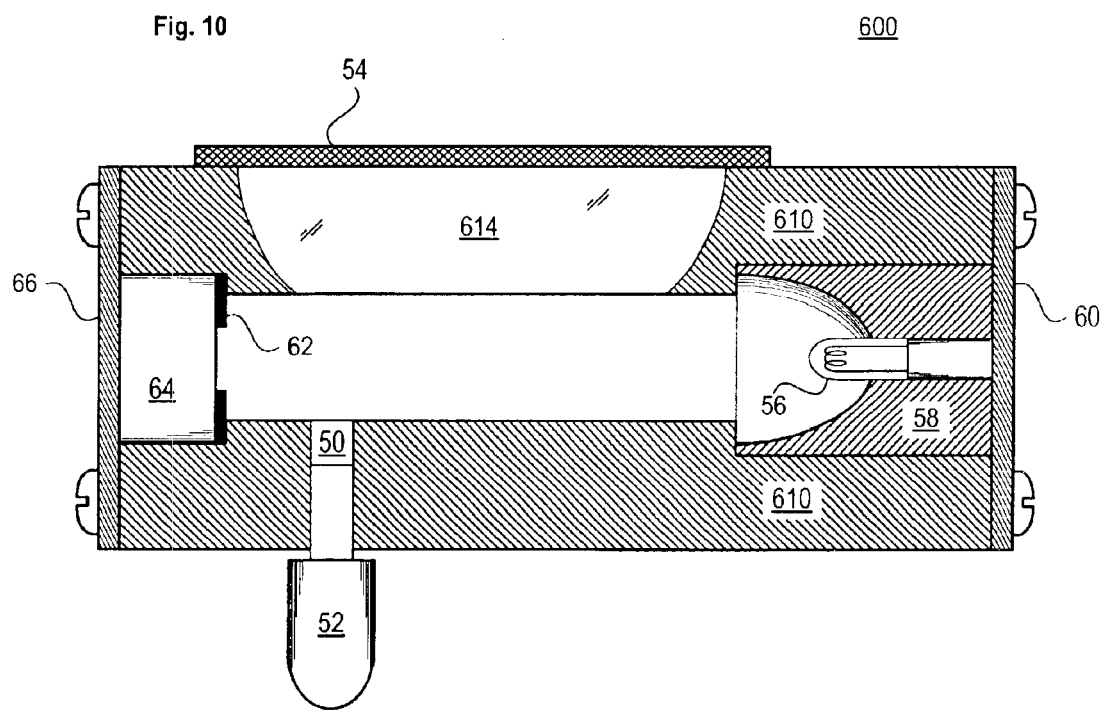
FIG. 10 shows, in long cross-section, another embodiment using a machined slot.

FIG. 10 shows a similar slot 514 used with a round chamber cross-section. Slot 514 enters the chamber as a groove with an opening in one sidewall, the base of the groove configured to generally reflect radiation down the chamber. Much of the light entering slot 514 strikes the base of the groove, and can be expected to reflect back out of the groove due to the angle of slot 514.

All of the slot shapes shown in the embodiments above are possible when formed as part of a chamber extrusion process. Other processes, such as machining, casting, or forging, can make the more simple slot shapes (or make slots that need not pass parallel to a direction of extrusion, nor extend along the entire length of the chamber). For instance, slot 614 of FIG. 10 is machined through the chamber wall, but stops short of the chamber ends.

Chambers can also be drilled into a chamber stock. Drilling can roughen the surface by creating circumferential scoring and a preferential roughening orthogonal to that obtained with extrusion, and therefore may have different spread reflection characteristics than those obtained with extruded chambers.

Although a 4:1 aspect ratio chamber has been depicted in the figures, the present invention is believed to be applicable to a large range of aspect ratios, from 2:1 on up to large aspect ratios for light-pipe style chambers.

One of ordinary skill in the art will recognize that the concepts taught herein can be tailored to a particular application in many other advantageous ways. For instance, the chamber need not have a rectangular cross-section, and in fact need not have a regular shape. Little attention has been paid to the usage of "wall" and "walls"—it is acknowledged that, except where a specific shape is specified, the claims are intended to cover single-walled and multi-walled chamber shapes. The source and detector need not be located all the way to the chamber ends-or both could be located at the same end, with a reflector at the opposite end. Although etching and yellow chromating are one way of roughening and passivating the chamber surface, other treatments could be used to produce similar results. The porous material, when used, does not have to be placed in direct contact with the slot, as long as the material is interposed between the chamber and potential sources of debris. Radiation wavelengths "of interest" depend on the specific sensor application. Such minor modifications are encompassed within the invention, and are intended to fall within the scope of the claims.

The preceding embodiments are exemplary. Although the specification may refer to "an", "one", "another", or "some" embodiment(s) in several locations, this does not necessarily mean that each such reference is to the same embodiment(s), or that the feature only applies to a single embodiment.

What is claimed is:

1. A gas sensor comprising:
   a sample chamber, at least twice as long in one dimension than in its other dimensions, measured internally, the chamber having a non-specular inner surface, compared to a radiation wavelength of interest, the chamber having a slot along the long dimension to allow gas to enter and exit the chamber, wherein the chamber is formed of an extruded stock material that contains, due to its manner of extrusion, both the slot and an inner surface that is preferentially roughened perpendicular to the long dimension of the chamber;
   a radiation source to omit electromagnetic radiation at least at the radiation wavelength of interest, arranged so as to project radiation along the long dimension of the sample chamber; and
   a radiation detector to detect electromagnetic radiation at least at the radiation wavelength of interest, arranged so as to receive radiation projected along the long dimension of the sample chamber.

2. The gas sensor of claim 1, the chamber having side walls at least half as thick as the chamber opening between those walls.

3. The gas sensor of claim 1, the chamber having a substantially uniform cross-section along its long dimension, the source and detector fixed near opposite ends of the long dimension of the chamber.

4. The gas sensor of claim 3, the source and detector fitted within the ends of the sample chamber, the slot extending over the source and detector.

5. The gas sensor of claim 3, the source having an incandescent bulb and an elliptical reflector, the bulb located inside the elliptical reflector near one focus of the ellipse, the second focus of the ellipse located within the sample chamber such that the reflector directs a substantial portion of the light it reflects from the bulb at the inner surface of the sample chamber.

6. The gas sensor of claim 3, further comprising an aperture stop between the detector and the chamber to limit the angles from which the detector can receive reflected radiation.

7. The gas sensor of claim 3, wherein the substantially uniform cross-section is square.

8. The gas sensor of claim 7, wherein the slot is centered along one wall of the square cross-section.

9. The gas sensor of claim 7, wherein the slot is offset, along one wall, towards a corner of the square cross-section.

10. The gas sensor of claim 9, wherein the slot enters the chamber at an angle such that radiation directed along the long dimension of the chamber that enters the slot strikes a wall of the slot and reflects back into the chamber and continues towards the detector.

11. The gas sensor of claim 1, wherein the sample chamber is formed of aluminum, the inner surface having a chromate coating.

12. The gas sensor of claim 1, wherein the slot enters the chamber at an angle such that radiation directed along the long dimension of the chamber that enters the slot strikes a wall of the slot and reflects back into the chamber and continues towards the detector.

13. The gas sensor of claim 1, wherein the slot, viewed depth wise, has a varying cross-section that is narrower at the inner chamber surface than at the outer chamber surface.

14. The gas sensor of claim 13, having a gas-permeable element, external to the chamber, which covers the slot.

15. A method of making a gas sensor chamber, comprising:
   extruding hollow chamber stock from a die to form, during stock extrusion, a slot connecting the interior of the chamber stock to the exterior of the chamber stock, under extrusion conditions that score the inner surface of the chamber stock, along the direction of extrusion, with features having peak-to-valley deviations greater than a radiation wavelength of interest; and
   passivating the inner surface of the chamber stock using a process that substantially preserves the extrusion features.

16. The method of claim 15, wherein passivating the inner surface comprises chemically etching the inner surface, and depositing a chromate layer on the etched surface.

17. The method of claim 15, wherein the die forms the slot with a narrower width at the inner surface of the chamber stock than at the outer chamber surface.

18. The method of claim 15, wherein the die forms the slot such that the slot enters the chamber at an angle other than normal to the inner chamber surface.

19. A method of making a gas sensor chamber, comprising extruding hollow chamber stock from a die to form a slot connecting the interior of the chamber stock to the exterior of the chamber stock, the die forming the slot at an angle to the inner chamber surface that allows radiation to be reflected off the side of the slot and back into the chamber.

20. A gas sample chamber comprising an elongated, hollow, lengthwise-slotted member, the slot having a depth-wise-varying width that is substantially narrower at the inner chamber surface than at the outer chamber surface, the slot angled with respect to the inner chamber wall adjacent the slot, such that radiation directed along the inner chamber that enters the slot is reflected back out of the slot and continues along the inner chamber.

21. A gas sample chamber comprising an elongated, hollow, lengthwise-slotted member, the slot angled with respect to the inner chamber wall adjacent the slot, such that radiation directed along the inner chamber that enters the slot is reflected back out of the slot and continues along the inner chamber.

22. A gas sensor comprising:
   a sample chamber, at least twice as long in one dimension than in its other dimensions, measured internally, the chamber having a slot along the long dimension to allow gas to enter and exit the chamber;
   a radiation source to emit electromagnetic radiation at least at the radiation wavelength of interest, arranged so as to project radiation along the long dimension of the sample chamber; and
   a radiation detector to detect electromagnetic radiation at least at the radiation wavelength of interest, arranged so as to receive radiation projected along the long dimension of the sample chamber;
   wherein the slot is configured to reflect at least a portion of electromagnetic radiation from the radiation source entering the slot back into the sample chamber such that the reflected radiation reaches the radiation detector.

* * * * *